(12) United States Patent
Burgi et al.

(10) Patent No.: US 9,119,731 B2
(45) Date of Patent: Sep. 1, 2015

(54) STRAIGHT CUP IMPACTOR

(75) Inventors: Jonas Burgi, Moutier (CH); Sarah Claude, La Chenalotte (FR)

(73) Assignee: Greatbach Medical S.A., Clarence, NY (US)

( * ) Notice: Subject to any disclaimer, the term of this patent is extended or adjusted under 35 U.S.C. 154(b) by 1116 days.

(21) Appl. No.: 13/007,735

(22) Filed: Jan. 17, 2011

(65) Prior Publication Data

US 2012/0184963 A1    Jul. 19, 2012

(51) Int. Cl.
*A61B 17/58*    (2006.01)
*A61F 2/46*    (2006.01)
*A61F 2/30*    (2006.01)

(52) U.S. Cl.
CPC ..... *A61F 2/4609* (2013.01); *A61F 2002/30566* (2013.01); *A61F 2002/4627* (2013.01); *A61F 2002/4629* (2013.01); *A61F 2002/4681* (2013.01)

(58) Field of Classification Search
CPC .................................................... A61F 2/4609
See application file for complete search history.

(56) References Cited

U.S. PATENT DOCUMENTS

| | | |
|---|---|---|
| 1,942,422 A | 6/1931 | Hanna |
| 4,305,394 A | 12/1981 | Bertuch, Jr. |
| D272,648 S | 2/1984 | Bolesky et al. |
| D273,806 S | 5/1984 | Bolesky et al. |
| 4,475,549 A | 10/1984 | Oh |
| 4,520,511 A | 6/1985 | Gianezio et al. |
| 4,528,980 A | 7/1985 | Kenna |
| 4,587,964 A | 5/1986 | Walker et al. |
| 4,632,111 A | 12/1986 | Roche |
| 4,716,894 A | 1/1988 | Lazzeri et al. |
| 4,765,328 A | 8/1988 | Keller et al. |
| 4,904,267 A | 2/1990 | Bruce et al. |
| 4,919,679 A | 4/1990 | Averill et al. |
| 4,921,493 A | 5/1990 | Webb, Jr. et al. |
| 5,019,105 A | 5/1991 | Wiley |
| 5,037,424 A | 8/1991 | Aboczsky |

(Continued)

FOREIGN PATENT DOCUMENTS

| | | |
|---|---|---|
| EP | 0453694 | 10/1991 |
| EP | 0470912 | 12/1992 |

(Continued)

OTHER PUBLICATIONS

European Search Report dated Apr. 15, 2011.

*Primary Examiner* — Nicholas Woodall
(74) *Attorney, Agent, or Firm* — Michael F. Scalise (57) ABSTRACT

A surgical tool device for effecting implantation of an implant such as an acetabular cup during a hip replacement surgery is described. The surgical tool holder has a strike plate, a body, a proximal fixed handle, a distal rotate handle, an insert handle with threads, an impactor head, a shaft, the shaft pin, a shaft ring, and a spring. In use, when a surgical implant device is threaded onto the shaft, the surgeon merely rotates the assembly comprising the distal rotate handle and the insert handle with threads in one direction, which causes a distal threaded area of the shaft to rotate in a second, opposite direction to act as a lock-nut for the surgical implant. This movement simultaneously pulls the shaft toward the surgical tool holder proximal end. The pulling motion ensures the surgical implant device is positioned against the impactor head's contacting surface to provide a rigid assembly for good tactile feel during the implantation of the cup.

18 Claims, 5 Drawing Sheets

(56) References Cited

U.S. PATENT DOCUMENTS

| | | |
|---|---|---|
| 5,061,270 A | 10/1991 | Aboczky |
| 5,062,854 A | 11/1991 | Noble et al. |
| 5,089,003 A | 2/1992 | Fallin et al. |
| 5,116,339 A | 5/1992 | Glock |
| 5,124,106 A | 6/1992 | Morr et al. |
| 5,133,766 A | 7/1992 | Halpern |
| 5,169,399 A | 12/1992 | Ryland et al. |
| 5,190,549 A | 3/1993 | Miller et al. |
| 5,234,432 A | 8/1993 | Brown |
| 5,261,915 A | 11/1993 | Durlacher et al. |
| 5,324,293 A | 6/1994 | Rehmann |
| 5,342,362 A | 8/1994 | Kenyon et al. |
| 5,364,403 A | 11/1994 | Petersen et al. |
| 5,417,696 A | 5/1995 | Kashuba et al. |
| 5,443,471 A | 8/1995 | Swajger |
| 5,454,815 A | 10/1995 | Geisser et al. |
| 5,485,887 A | 1/1996 | Mandanis |
| 5,540,697 A | 7/1996 | Rehmann et al. |
| 5,584,837 A | 12/1996 | Petersen |
| 5,658,294 A | 8/1997 | Sederholm |
| 5,665,091 A | 9/1997 | Noble et al. |
| 5,683,399 A | 11/1997 | Jones |
| 5,707,374 A | 1/1998 | Schmidt |
| 5,720,750 A | 2/1998 | Koller et al. |
| 5,863,295 A | 1/1999 | Averill et al. |
| 5,913,860 A | 6/1999 | Scholl |
| 5,976,148 A | 11/1999 | Charpenet et al. |
| 5,993,455 A | 11/1999 | Noble |
| 6,063,124 A | 5/2000 | Amstutz |
| 6,120,508 A | 9/2000 | Grunig et al. |
| 6,197,065 B1 | 3/2001 | Martin et al. |
| 6,432,141 B1 | 8/2002 | Stocks et al. |
| 6,451,058 B2 | 9/2002 | Tuke et al. |
| 6,626,913 B1 | 9/2003 | McKinnon et al. |
| 6,663,636 B1 | 12/2003 | Lin |
| 6,811,569 B1 | 11/2004 | Afriat et al. |
| 7,192,449 B1 | 3/2007 | McQueen et al. |
| 7,341,593 B2 | 3/2008 | Auxepaules et al. |
| 7,396,357 B2 | 7/2008 | Tornier et al. |
| 7,585,301 B2 | 9/2009 | Santarella et al. |
| 7,591,821 B2 | 9/2009 | Kelman |
| 7,604,667 B2 | 10/2009 | DeSmet et al. |
| 7,621,921 B2 | 11/2009 | Parker |
| 7,922,726 B2 | 4/2011 | White |
| 2001/0051830 A1 | 12/2001 | Tuke et al. |
| 2002/0004660 A1 | 1/2002 | Henniges et al. |
| 2002/0116007 A1 | 8/2002 | Lewis |
| 2002/0177854 A1 | 11/2002 | Tuke et al. |
| 2002/0193797 A1 | 12/2002 | Johnson et al. |
| 2003/0009234 A1 | 1/2003 | Treacy et al. |
| 2003/0050645 A1 | 3/2003 | Parker et al. |
| 2003/0083668 A1 | 5/2003 | Rogers et al. |
| 2003/0088316 A1 | 5/2003 | Ganjianpour |
| 2003/0187512 A1 | 10/2003 | Frederick et al. |
| 2003/0220698 A1 | 11/2003 | Mears et al. |
| 2003/0229356 A1 | 12/2003 | Dye |
| 2004/0215200 A1 | 10/2004 | Tornier et al. |
| 2005/0038443 A1 | 2/2005 | Hedley et al. |
| 2005/0075736 A1 | 4/2005 | Collazo |
| 2005/0137603 A1 | 6/2005 | Belew et al. |
| 2005/0171548 A1 | 8/2005 | Kelman |
| 2005/0187562 A1 | 8/2005 | Grimm et al. |
| 2005/0222572 A1 | 10/2005 | Chana |
| 2005/0228395 A1 | 10/2005 | Auxepaules et al. |
| 2005/0234462 A1 | 10/2005 | Hershberger |
| 2005/0246031 A1 | 11/2005 | Frederick et al. |
| 2006/0052780 A1 | 3/2006 | Errico et al. |
| 2006/0149285 A1 | 7/2006 | Burgi et al. |
| 2007/0156155 A1 | 7/2007 | Parker |
| 2007/0167952 A1 | 7/2007 | Burgi et al. |
| 2007/0225725 A1 | 9/2007 | Heavener et al. |
| 2007/0270783 A1 | 11/2007 | Zumsteg et al. |
| 2007/0288096 A1 | 12/2007 | Surma |
| 2007/0293869 A1 | 12/2007 | Conte et al. |
| 2008/0004628 A1 | 1/2008 | White |
| 2008/0021481 A1 | 1/2008 | Burgi |
| 2008/0033444 A1 | 2/2008 | Bastian et al. |
| 2008/0077249 A1 | 3/2008 | Gradel |
| 2008/0146969 A1 | 6/2008 | Kurtz |
| 2008/0154261 A1 | 6/2008 | Burgi |
| 2008/0243127 A1 | 10/2008 | Lang et al. |
| 2008/0255565 A1 | 10/2008 | Fletcher |
| 2008/0255568 A1 | 10/2008 | Tornier et al. |
| 2008/0262503 A1 | 10/2008 | Muller |
| 2008/0275450 A1 | 11/2008 | Myers et al. |
| 2009/0112214 A1 | 4/2009 | Philippon et al. |
| 2009/0182334 A1 | 7/2009 | Brehm |
| 2009/0192515 A1 | 7/2009 | Lechot et al. |
| 2009/0240256 A1 | 9/2009 | Smith |
| 2009/0281545 A1 | 11/2009 | Stubbs |
| 2014/0114321 A1* | 4/2014 | Davenport et al. ............. 606/91 |

FOREIGN PATENT DOCUMENTS

| | | |
|---|---|---|
| EP | 0535973 | 4/1993 |
| EP | 357302 | 7/1994 |
| EP | 638299 | 2/1995 |
| EP | 1308140 | 5/2003 |
| EP | 1190687 | 7/2004 |
| EP | 1438936 | 7/2004 |
| EP | 1447058 | 8/2004 |
| WO | 9511641 | 5/1995 |
| WO | 0012832 | 3/2000 |
| WO | 0106964 | 2/2001 |
| WO | 2005044153 | 5/2005 |
| WO | 2006061708 | 6/2006 |
| WO | 2007098549 | 9/2007 |
| WO | 2008128282 | 10/2008 |
| WO | 2009136284 | 11/2009 |

* cited by examiner

FIG. 6 stry # STRAIGHT CUP IMPACTOR

FIELD OF THE INVENTION

The invention relates to surgical tools for aiding a surgeon installing orthopedic prostheses in patients.

BACKGROUND OF THE INVENTION

A total hip replacement is a reconstructive surgical procedure performed by an orthopedic surgeon and the surgeon team. A total hip replacement involves the placement of an acetabular cup in a patient's acetabular socket, and the replacement of the patient's femoral neck with a prosthesis which terminates in a ball specifically designed to be positioned in the acetabular cup. Other surgical procedures may require the application of an acetabular cup or other device applied to a patient.

For example during such acetabular cup procedures, the patient's acetabular socket is reamed out by the surgeon so as to create an enlarged recess to receive the acetabular cup. After the acetabular socket has been reamed, the cup is inserted into the recess and adjusted as necessary to the proper angular orientation. Once deployed, the cup provides a new socket and lining for the patient's acetabulum.

Insertion and placement of the cup by the surgeon is effected either by hand or by use of a hand tool that grips the cup. Once the cup is properly positioned in the acetabulum, the cup can be fixed in the desired location by various means—bone screws, medically acceptable adhesives, or combinations thereof. In many instances, the fixation means include passing bone screws through the cup and into pre-drilled screw holes in the pelvic bone. The bone screws, which are optional, serve to hold the acetabular cup in the acetabulum until bone ingrowth provides permanent fixation.

In one acceptable medical method, the cup is properly positioned in the acetabulum by implantation. One conventional implantation method is, after obtaining proper alignment, to impact an acetabular cup into place. While impacting the acetabular cup, the surgeon listens for a change in pitch as the cup seats down. The surgeon then probes screw holes to determine if a gap between the cup and the bone is present. If a gap is present, the surgeon further impacts the cup into the acetabulum.

Figure 1:
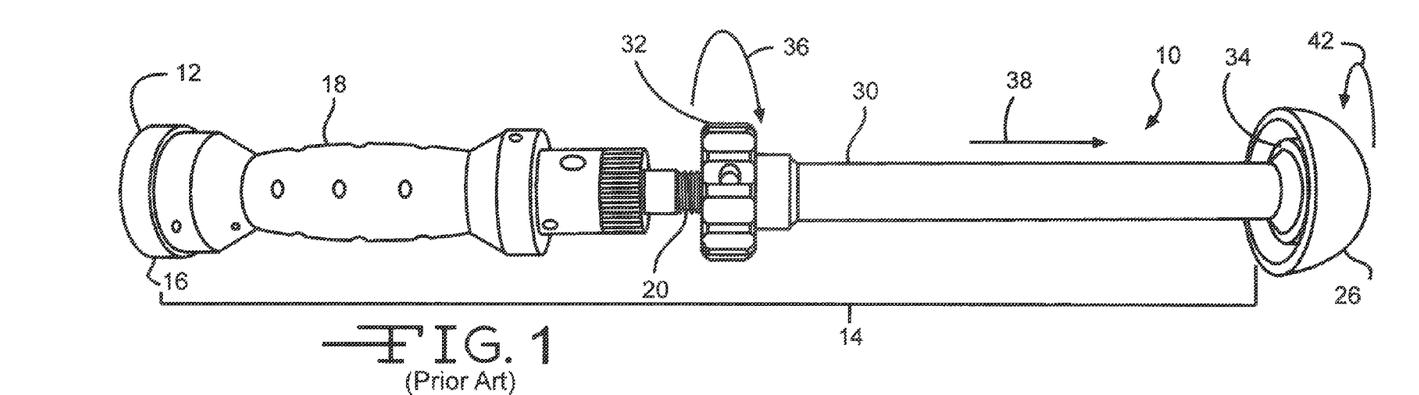
FIG. 1 is a prior art illustration of an alternative spindle-type surgical tool.
Figures 2, 2A:
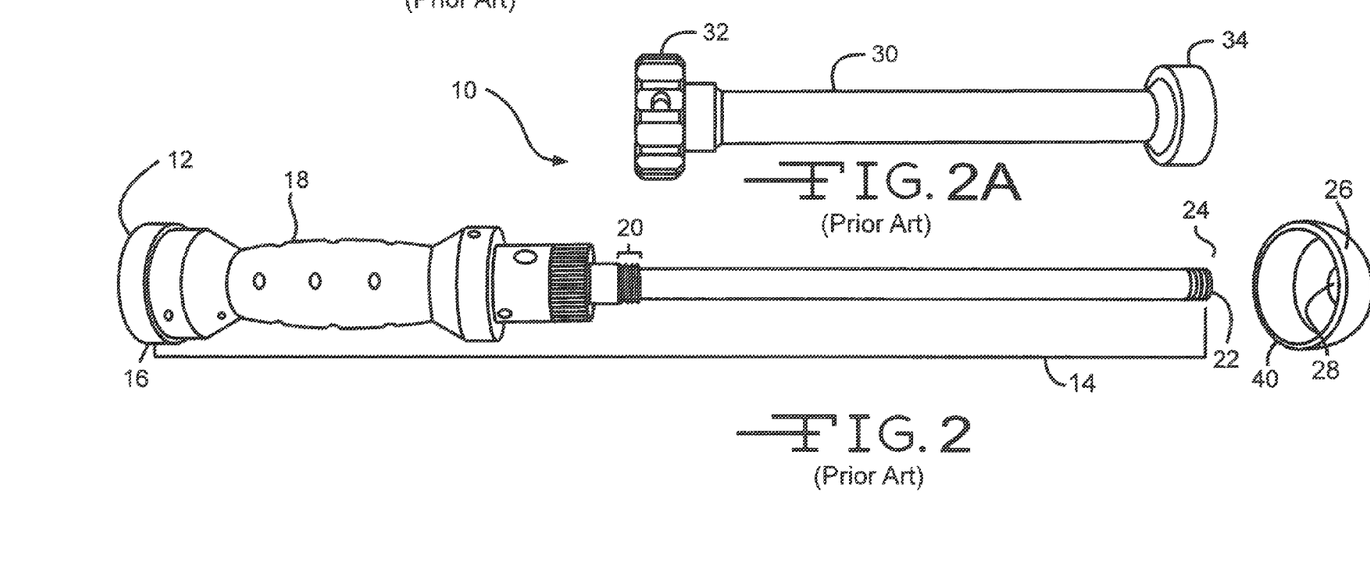
FIG. 2 illustrates the handle 18 and connected body portion 14 of the prior art device of FIG. 1.
FIG. 2A illustrates the prior art handle device 30 of FIG. 1.

As illustrated in FIGS. 1 and 2, a conventional spindle-type surgical tool holder has a strike plate 12 integrally connected to a body's 14 proximal end 16. Extending from the strike plate 12 and positioned over a proximal area of the body portion 14 is a fixed handle 18. The fixed handle 18 has a length that allows a surgeon to hold the tool holder 10, in one embodiment with one hand, and in an alternative embodiment with two hands. Whatever the fixed handle's 18 length, extending there from on the body 14 is an impactor thread section 20. At the body portion's distal end 22 is a tool thread section 24.

The tool thread section 24 threadingly interconnects to a surgical implant device (a.k.a., medical attachment) 26, for example, and not limited to, an acetabular cup, through a threaded aperture 28 (FIG. 2). That means the implant device 26 is directly connected to the body 14 and the strike plate 12. To ensure the surgical implant device 26 is properly secured to the tool thread section 24, the prior art device 10 uses a rotate handle device 30 (FIG. 2A).

The rotate handle 30 is positioned in the spacing between the tool thread section 24 and the impactor thread section 20. At its proximal end, the rotate handle device 30 has a rotating threaded section 32 and at its distal end, an implant support 34. The rotating threaded section 32 has threads that mate with the impactor thread section 20. When the rotating threaded section 32 is rotated clockwise (illustrated by arrow 36 at FIG. 1), (a) the rotating threaded section 32 pushes (illustrated by arrow 38) the rotate handle 30 and the implant support surface 34 toward the surgical implant device's interior surface 40 (FIG. 2); and (b) simultaneously, the rotating threaded section 32, through a conventional lock-nut structure, rotates the surgical implant device 26 counter-clockwise (arrow 42 at FIG. 1). This movement results in the surgical implant 26 being pushed toward the implant support 34. Collectively, the clock-wise rotating threaded section 32 is designed to securely position the surgical implant 26 against the implant support 34 to inhibit dislodging of the surgical implant device 26 from the spindle-type tool holder 10 when the surgeon impacts the tool holder.

However, when the surgeon impacts the strike plate 12 there is a chance that the surgical implant 26 can disconnect from the tool holder 10. This could occur when the tool holder's 10 threaded section 24 or the implant's 26 corresponding threaded section 26 are damaged, possibly by the act of impaction. Accordingly, what is needed is a firm fixation of the surgical implant 26 during impaction that provides minimal damage to the implant's 26 threads 28. That desired product is achieved with the current invention.

SUMMARY OF THE INVENTION

The surgical tool handling device of the present invention has both non-moving and moving components during connection to an implant after the implant cup seats. However, during impaction, the entire surgical device is static or rigid. Having both moving and non-moving parts ensures a stable threaded connection between the surgical tool and the implantable cup.

DETAILED DESCRIPTION OF THE INVENTION

Figure 3:
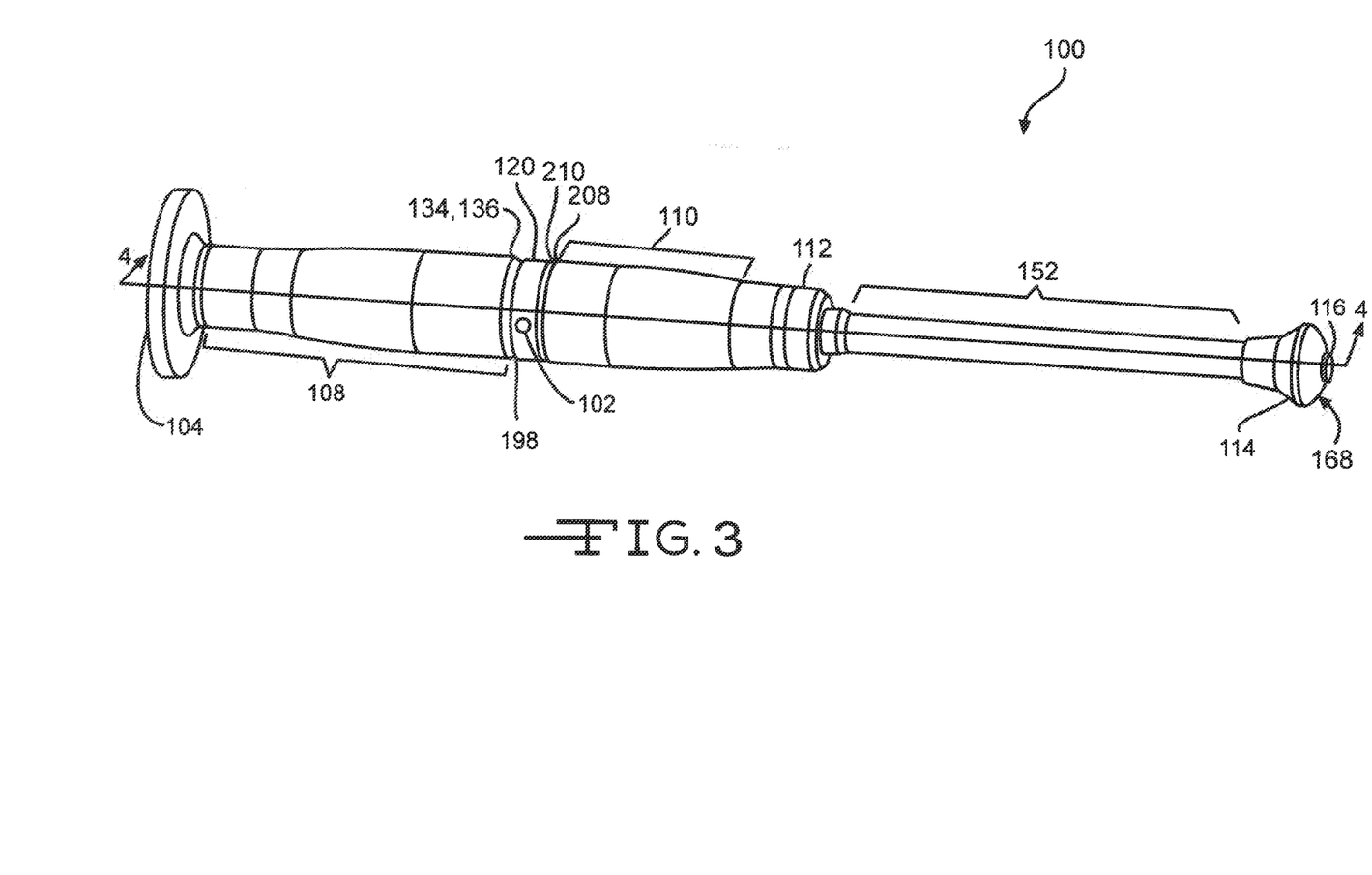
FIG. 3 illustrates the exterior surface of the spindle-type surgical tool holder of the present invention.
Figure 4:
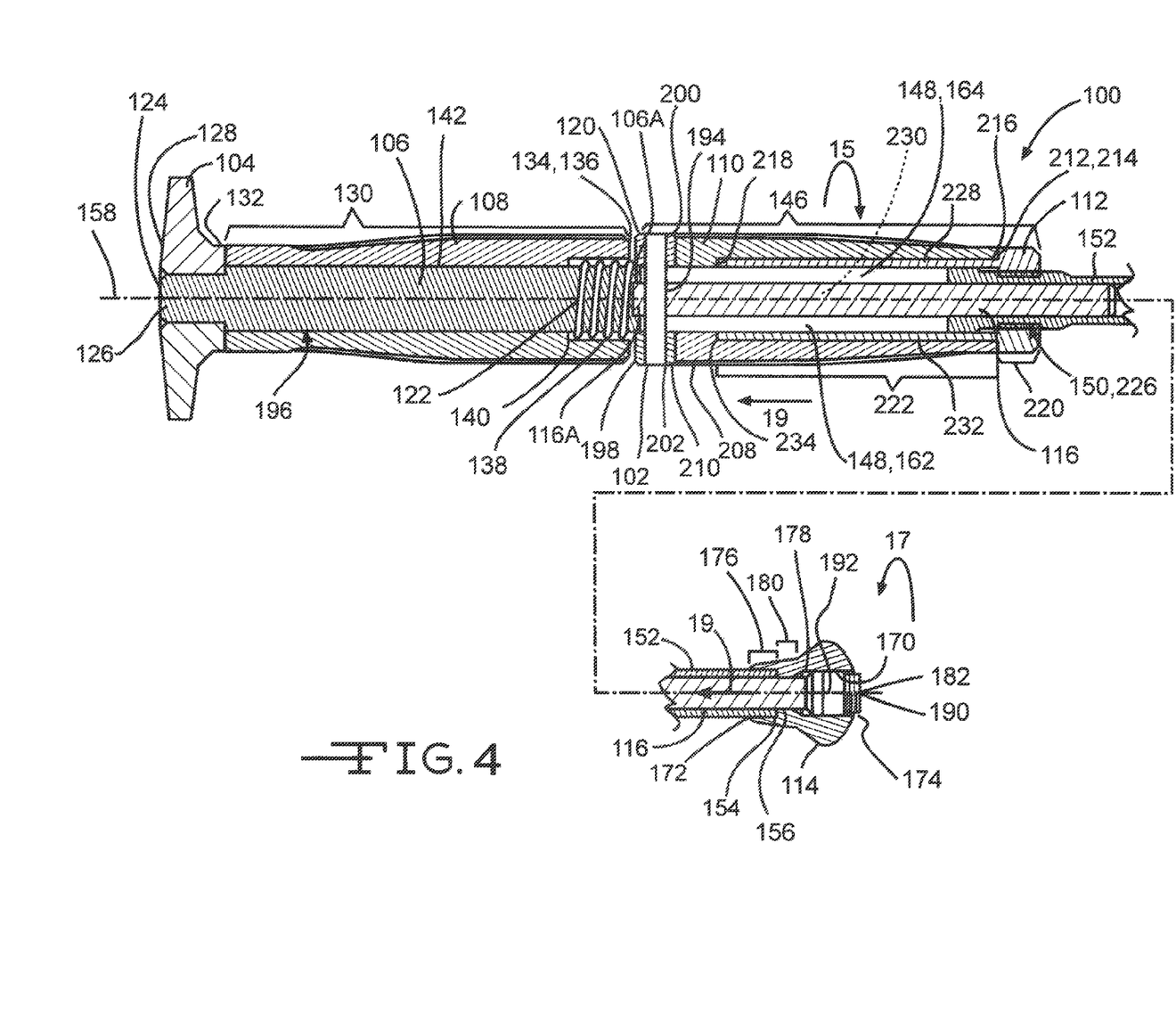
FIG. 4 illustrates a cross-sectional view of FIG. 3 taken along the lines 4-4 and rotated 90 degrees.
Figure 5:
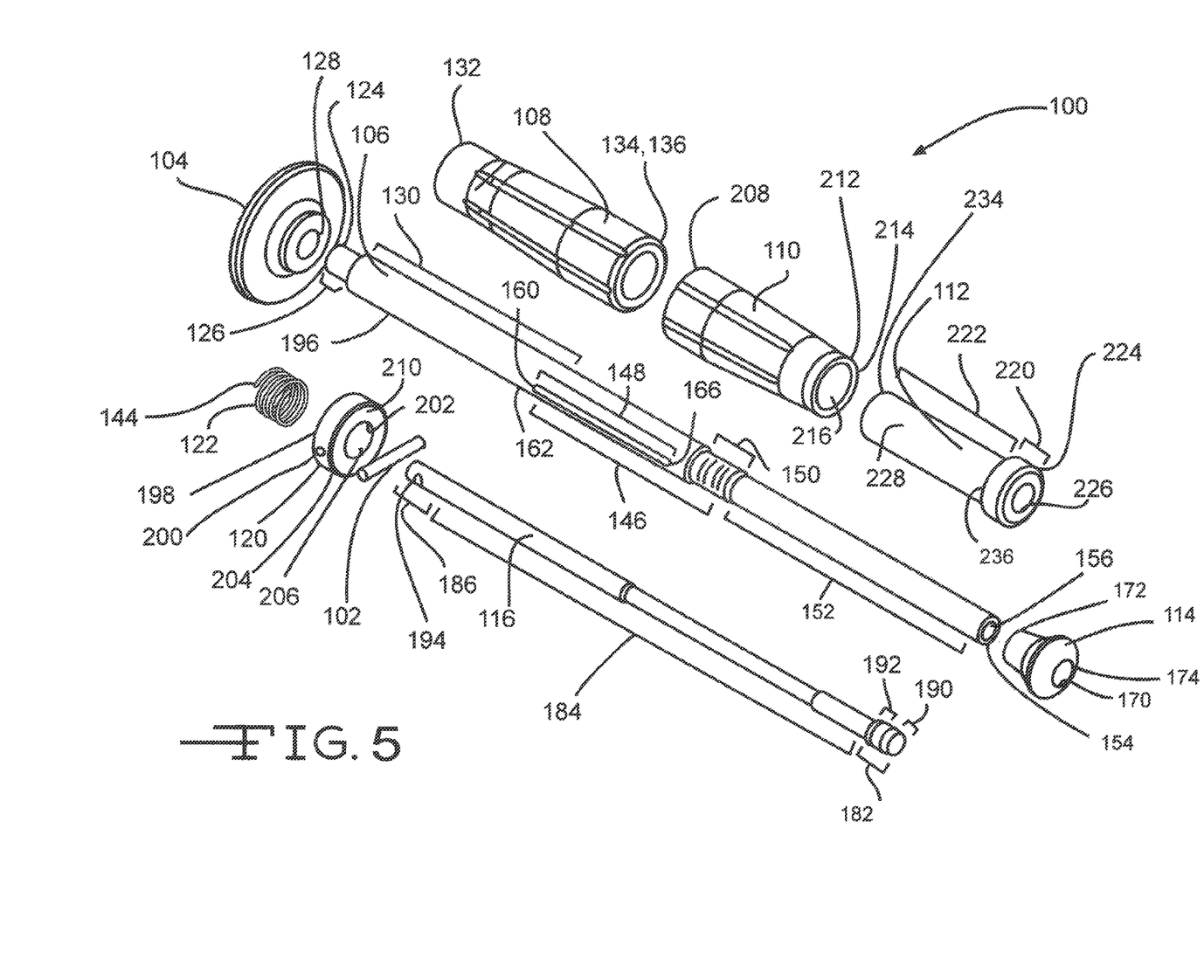
FIG. 5 illustrates an exploded view of FIG. 3.

FIGS. 3, 4 and 5 illustrate an improved spindle-type surgical tool holder 100 according to the present invention. FIG. 3 illustrates the exterior surface of the tool holder 100; FIG. 4 illustrates a cross-sectional view of FIG. 3 taken along the lines 4-4 and rotated 90 degrees so that shaft pin 102 is vertical instead of horizontal as in FIG. 3; and FIG. 5 illustrates an exploded view of FIG. 3. From that general understanding of FIGS. 3 to 5, we will discuss the spindle-type surgical tool holder 100.

The improved spindle-type surgical tool holder 100 has a strike plate 104, a proximal shaft 106, a proximal fixed handle 108, a distal rotate handle 110, an insert handle with threads 112, an impactor head 114, a distal shaft 116, the shaft pin 102, a shaft ring 120, and a spring or any other conventional resilient member 122 (seen in FIGS. 4 and 5).

The strike plate 104 connects to the proximal end 124 of the proximal shaft 106. As illustrated, the strike plate 104 is press-fitted, welded, or by any other conventional means is securely attached to the proximal shaft 106; or alternatively, is an integral part of the shaft 106. In the embodiment illustrated in FIGS. 4 and 5, the proximal shaft 106 has a strike plate extension 126 at its proximal end 124 that press fits within the strike plate's female aperture 128. In any embodiment, the strike plate 104 is securely attached to the proximal shaft 106 in such a way that the strike plate 104 is not easily removed, under normal operating conditions for the surgical tool holder.

The proximal fixed handle 108 extends from the strikeplate 104 and is positioned over the proximal shaft 106 (FIGS. 4 to 5). The proximal fixed handle 108, as with the prior art tool holder 10, has a length that allows a surgeon to hold it, in one embodiment with one hand, and in an alternative embodiment with two hands. The fixed handle's 108 proximal end 132, in a preferred embodiment, contacts the strike plate 104. The fixed handle's 108 distal end 134 has a ring stopper distal end 136 (FIGS. 3, 4 and 5), an internal spring cavity 138, a spring abutment 140 and an internal body cavity 142. The body cavity 142 extends from the spring abutment 140 to the proximal end 132 and has a diameter that allows the fixed handle 108 to be positioned over and preferably contact the proximal shaft 106. The spring cavity 138 is an opening adjacent to the cavity 142 that receives the proximal shaft 106 and the spring 122 so the spring 122 can expand and contract depending on the force applied to it. The spring's tension force is sufficient to ensure that the surgical implant device 26 is securely attached, when desired, to the surgical tool holder 100. The spring abutment 140 is where the spring's proximal end 144 contacts the fixed handle 108.

As illustrated in FIGS. 4 and 5, the tool holder 100 has numerous sections. The first section is the strike plate extension 126 which has already been discussed. The second section is the fixed handle area 130 which has also been discussed. The third section is a rotating handle 110/ring 120 area 146 (FIG. 5). Within the rotating handle 110/ring 120 area 146, and in some embodiments an overlap in the fixed handle area 130, is a slot area 148 (FIGS. 4 and 5). Also within the rotating handle/ring area 146 and at its distal end is a distal rotating thread area 150. A fourth section is an insertion area 152 that extends to the distal end 154 of the tool holder 100.

Starting at the distal end 154, the insertion area 152 has a cavity 156 of a diameter greater than the outer diameter of the distal shaft 116. That is so the distal shaft 116 can move in the cavity 156 along the rotate handle's and cavity's co-longitudinal axis 158 (FIG. 4). The cavity 156 extends proximally beyond the proximal end 160 (FIG. 5) of the slot area 148.

The slot area 148 contains a first axial opening 162 (FIGS. 4 and 5) and, in most embodiments, a second axial opening 164 (FIG. 4) that is diametrically opposed to the first opening 162. The first and second axial openings 162, 164 receive the opposed ends of the shaft pin 102. Each axial opening 162, 164 has a predetermined length that allows the shaft pin 102, the distal shaft 116, and the shaft ring 120 to move a predetermined distance along the spindle's axis 158 to allow the surgical tool holder 100 to be easily cleaned, but securely attached to a surgical implant 26.

The distal rotating threaded area 150 is spaced a predetermined distance from the slot area's 148 distal end 166. That distance depends on the lengths of the distal rotate handle 110 and the insert handle with threads 112. The rotating thread area 150 has threads that mate with corresponding threads on the insert handle 112. The rotating thread area 150 has a length that allows the insert handle 112 to be rotated, through the distal rotate handle 110, to properly position the shaft ring 120, the distal shaft 116, and the surgical implant device 26 in order to decrease the chance of damaging or displacing the surgical implant 26 from the holder 100 during the surgical operation.

Extending from the distal rotating thread area 150 toward the distal end 154 is the insertion area 152. The insertion area 152 can be any desired length that assists and allows the surgeon to properly use the spindle-type surgical tool holder 100. Attached to the insertion area's distal end 154 is the impactor head 114.

The impactor head 114 has a contacting surface 168 (FIG. 3), and a second cavity 170 that extends from the head's proximal end 172 to its distal end 174 along a second longitudinal axis, which is co-axial with the longitudinal axis 158. The second cavity 170 has three sections as illustrated at FIG. 4. They are a body cavity 176, a tip cavity 178, and an interference fit cavity 180. The body cavity 176 has a first diameter that receives the insertion area's distal end 154 and a length that impairs the impactor head 114 from disconnecting from the insertion area's distal end 154.

The interference fit cavity 180 has a second diameter, smaller than the first body cavity diameter, which receives the distal shaft 116, but not the insertion area's distal end 154. The shaft 116 is capable of movement along the interference fit cavity. The interference fit cavity 180 also creates an obstacle that inhibits the threaded distal end 182 of the distal shaft 116 from entering the body cavity 176. The tip cavity 178 has a third diameter, greater than the second diameter, and equal to, smaller than, or greater than the first diameter. The third diameter is sufficient to allow the distal shaft's 116 threaded distal end 182 to move therein and extend from the head's distal end 174.

The contacting surface 168 is at the head's distal end 174. The contacting surface 168 is designed to contact the interior surface of the surgical implant 26 (similar to how the prior art's implant support 34 operates). In that respect, the contacting surface 168 is designed to provide an additional stabilization surface to the surgical implant device 26 during the surgical procedure and to inhibit the implant 26 from disconnecting from the spindle-type surgical tool holder 100.

As shown in FIG. 5, the distal shaft 116 has three sections. They are the partially threaded distal end 182, an elongated intermediate section 184, and a proximal pin section 186. The threaded distal end 182 has at least a distal threaded area 190 having a first shaft diameter and an implant stopper area 192 having a second diameter, greater than or equal to the first shaft diameter. The distal threaded area 190 is designed to be threaded into the threaded aperture 28 of the surgical implant 26. Likewise, the implant stopper area 192 is designed to inhibit the surgical implant 26 from penetrating beyond the proximal end of the distal threaded area 190.

Extending in the proximal direction of the distal shaft 116 from the partially threaded distal end 182 is the elongated intermediate section 184. The elongated intermediate section 184 can be a single diameter or multiple diameters (as illustrated in FIGS. 4 and 5). In any event, the elongated intermediate section's diameter, which is smaller than that of the shaft cavity 156, enables movement of the elongated intermediate section 184 of the distal shaft 116 along the longitudinal axis 158 of the cavity 156 and the distal rotate handle.

Adjacent to the distal shaft's 116 proximal end is the pin section 186. The pin section 186 has a shaft pin aperture 194 that extends from one side to the opposing side of the shaft as illustrated in FIGS. 4 and 5; but alternatively the aperture 194 could just be on the shaft's one side. While in the body's cavity, the shaft pin aperture 194 is aligned with the first and/or second axial openings 162 and 164 in the slot area 148.

The shaft pin aperture 194 has a diameter that receives and, possibly, secures the shaft pin 102 in place. This aperture and pin relationship can be a loose fit, a press-fit, a conventional rib and indent system, a conventional spring-loaded ball and indent system, or any functionally equivalent system that fixedly attaches the pin in the aperture or securely attaches, and also allows the release of, the pin in the aperture, or alternatively allows the pin 102 to move freely within the pin aperture 194. The aperture and pin relationship depends on how the pin 102 is used in association with other components of the present invention. For example, if there is no shaft ring 120, the pin and aperture have to be permanently attached or securely attached. Likewise, if there is a shaft ring 120, then the pin and aperture can be any of the three possible attachment embodiments especially if the shaft ring and the pin are securely attached to each other.

Prior to inserting the pin 102 in the shaft pin aperture 194 and through the shaft's first and second axial openings 162 and 164, the shaft ring 120 is properly positioned on the shaft's exterior surface 196. As previously stated, the spring 122 is positioned in the fixed handle's 108 spring cavity 138 with its proximal end 144 contacting the spring abutment 140. Likewise, the proximal end 198 of the shaft ring 120, preferably contacts the fixed handle's ring stopper distal end 136. In addition, the shaft ring 120 has one or, preferably, two ring pin apertures 200, 202 that are diametrically opposed to each other. Each ring pin aperture extends from the shaft ring's outer surface 204 to its respective inner surface 206 and has a diameter that receives and secures the pin 102 in place. The ring pin apertures 200, 202 and shaft pin 102 relationship can be a press-fit, a rib and indent system, a spring-loaded ball and indent system, or any functionally equivalent system that either permanently attaches the shaft pin in the ring pin apertures 200, 202 or securely attaches, and also allows the release of, the pin 102 in the apertures. As expected, the ring pin apertures 200, 202, the shaft pin aperture 194 and the shaft's 116 first and second axial openings 162 and 164 must be aligned to receive the shaft pin 102.

Prior to or after the shaft pin 102 is properly positioned and secured in the ring pin apertures 200, 202, the shaft pin aperture 194 and the first and second axial shaft openings 162 and 164, and the rotate handle 110 are positioned over a portion of the exterior surface of the insert handle with threads 112. This assembly is then positioned over the rotating handle 110/ring 120 area's 146 exterior surface. The distal rotating handle 110 has a proximal end 208 that contacts the distal end 210 of the shaft ring 120, and a distal end 212. The distal end 212 has a threaded insert handle stopper 214, an insert handle cavity 216 (FIGS. 4 and 5) that extends to the proximal end 208, and an insert handle cavity stopper 218 (FIG. 4).

The insert handle with threads 112 has a distal threaded area 220 and a proximal rotating area 222. The threaded area 220 has an outer diameter 224 (FIG. 5) and an inner threaded diameter 226 (FIGS. 4 and 5). The inner threaded diameter 226 has threads that threadingly engage with the distal shaft's 116 rotating thread area 150. The proximal rotating area 222 has an outer diameter 228, preferably smaller than the threaded area's outer diameter 224, and an inner diameter 230. In order for the proximal rotating area 222 to freely rotate, the inner diameter 230 is greater than the outer diameter 232 of the distal shaft 116. The insert handle cavity 216 receives the rotating area 222 of the insert handle with threads 112 so that its proximal end 234 contacts the insert handle cavity stopper 218; and the threaded area's 220 proximal end 236 contacts the threaded insert handle stopper 214.

In use, when a surgical implant device 26 is threaded onto the shaft's threaded area 190, the surgeon merely rotates the assembly comprising the distal rotate handle 110 and the insert handle with threads 112 in one direction, normally clockwise (see arrow 15 in FIG. 4). This movement causes the distal threaded area 190 of the distal shaft 116 to rotate in a second, opposite direction, normally counterclockwise (see arrow 17), to thereby act as a locknut for the surgical implant 26. This movement simultaneously pulls the distal shaft 116 (see arrow 19 in FIG. 4) toward the spindle-type surgical tool holder 100 proximal end 124. The pulling motion ensures the surgical implant device is positioned against the impactor head's contacting surface 168.

Then, in order to position an implant 26 in an acetabulum, an axial force is imparted to the strike plate 104 connected to the proximal shaft 106. The proximal shaft 106 housed inside the proximal fixed handle 108 is, in turn, rigidly connected to the distal shaft 116 having its proximal end 116A seated in a distal recess 106A of the proximal shaft 106. The opposite, distal end of the distal shaft 116 is threaded into the implant 26. That way, the entire assembly is static or rigid with the implant attached held firmly against impactor head 114. This provides a good tactile feel to the surgeon as the force imparted to the strike plate 104 translates through the tool holder 100 to effect implantation of the cup 26.

Figure 6:
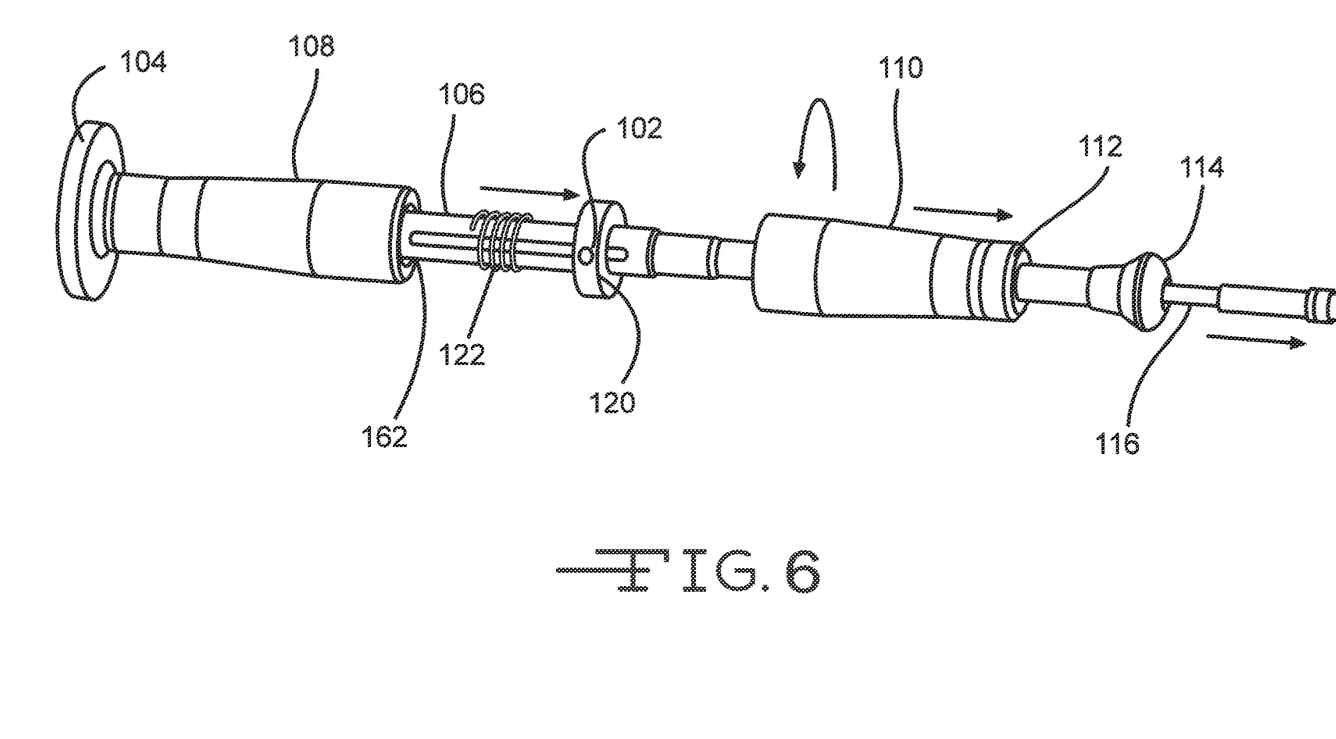
FIG. 6 illustrates FIG. 3 expanded for cleaning purposes.

As illustrated at FIG. 6, cleaning of the claimed spindle-type surgical tool holder 100 is also relatively easy. First, the user disengages the inner threaded diameter 226 from the shaft's rotating thread area 150. Second, the user pulls all the moving components toward the holder's distal end, to expose them for easy cleaning.

Although several embodiments of the invention have been described in detail for purposes of illustration, various modifications of each may be made without departing from the spirit and scope of the invention. For example, there can be just one opening or a plurality of openings for the slot area. The shaft pin may only extend from one opening or two openings. In addition, there may be numerous shaft pins extending from one opening or two openings in the slot area. The resilient member can be a spring of any conventional resilient object made of metal, plastic, or a gelatinous elastomeric material made from an A-B-A triblock copolymer. Examples of A-B-A triblock copolymers are SEP, SEB, SEBS, SEEPS ("S" is styrene monomer(s), "E" is ethylene monomer(s), "B" is butylene monomer(s), and "P" is propylene monomer(s)) and variations thereof made by the Kuraray Corporation. The directions of clockwise and counterclockwise can be transposed depending on the thread types. Depending on the shape of the shaft pin, the shaft ring is optional. Accordingly, the invention is not limited, except by the appended claims.

What is claimed is:

1. A surgical tool handle, which comprises:
   a) a fixed handle comprising a first length extending along a longitudinal axis from a fixed handle proximal end to a fixed handle distal end, wherein an axial cavity extends along the longitudinal axis in a proximal direction from the fixed handle distal end at least part way along the first length thereof;
   b) a second shaft comprising a second length extending along the longitudinal axis from a second shaft proximal portion received in the axial cavity to a second shaft distal portion extending out beyond the axial cavity of the distal end of the fixed handle, wherein the second shaft includes a first axial slot having a third length that is shorter than the second length with the slot not extending to a distal end of the second shaft but extending inwardly from an outer surface thereof and being in open communication with a first axial bore extending to the distal end of the second shaft, wherein at least the second shaft distal portion has a threaded exterior surface;

c) a coil spring received in an annular space provided between the outer surface of the second shaft proximal portion received in the axial cavity and an inner surface of the fixed handle;

d) an inner shaft extending through the first axial bore in the second shaft from an inner shaft proximal end to a threaded distal end configured to support a prosthesis, wherein the proximal end of the inner shaft supports a radial pin that is axially moveable along the slot in the second shaft such that when the radial pin biases against the coil spring, the distal threaded end of the inner shaft extends axially out beyond the distal end of the second shaft; and e) a rotatable handle comprising a third axial bore extending along the longitudinal axis from a rotatable handle proximal end to a rotatable handle distal end, wherein the rotatable handle has a threaded inner surface that threading engages with the external threads of the second shaft, f) wherein when the rotatable handle is rotated in a first direction with the rotatable threads threadingly engaging the external threads of the second shaft, the rotatable handle moves proximally along the longitudinal axis to thereby cause the inner shaft to move in a proximal direction against the bias of the coiled spring and to simultaneously move the distal threaded end of the inner shaft closer to the distal portion of the second shaft, and g) wherein when the rotatable handle is rotated in a second, opposite direction, the rotatable threads threadingly disengage from the external threads of the second shaft as the rotatable handle moves distally along the longitudinal axis to thereby lessen the bias between the radial pin and the coil spring so that the threaded distal end of the inner shaft is movable in a distal direction to increase a distance between the distal portion of the second shaft and the distal threads of the inner shaft.

2. The surgical tool handle of claim 1 wherein a distal end of the axial pin is connected to a shaft ring positioned between the fixed handle and the rotatable handle.

3. The surgical tool handle of claim 1 further comprising a strikeplate at the proximal end of the fixed handle.

4. The surgical tool handle of claim 1 wherein the intermediate shaft has a second axial slot and the radial pin is movable along both the first and second radial slots.

5. The surgical tool handle of claim 4 wherein the second axial slot is diametrically opposed to the first axial slot.

6. The surgical tool handle of claim 1 wherein the distal end of the intermediate shaft has a larger diameter than an inner diameter of the threaded inner surface of the rotatable handle.

7. The surgical tool handle of claim 1 wherein the second shaft distal portion supports an impactor head.

8. A method of using a surgical tool handle, comprising the steps of:
a) providing a surgical tool comprising:
i) a fixed handle comprising a first length extending along a longitudinal axis from a fixed handle proximal end to a fixed handle distal end, wherein an axial cavity extends along the longitudinal axis in a proximal direction from the fixed handle distal end at least part way along the first length thereof;

ii) a second shaft comprising a second length extending along the longitudinal axis from a second shaft proximal portion received in the axial cavity to a second shaft distal portion extending out beyond the axial cavity of the distal end of the fixed handle, wherein the second shaft includes an axial slot having a third length that is shorter than the second length with the slot not extending to a distal end of the second shaft but extending inwardly from an outer surface thereof and being in open communication with an axial bore extending to the distal end of the second shaft, wherein at least the second shaft distal portion has a threaded exterior surface;

iii) a coil spring received in an annular space provided between the outer surface of the second shaft proximal portion received in the axial cavity and an inner surface of the fixed handle;

iv) an inner shaft extending through the axial bore in the second shaft from an inner shaft proximal end to a threaded distal end configured to support a prosthesis, wherein the proximal end of the inner shaft supports a radial pin that is moveable along the axial slot in the second shaft such that when the radial pin biases against, the coil spring, the distal threaded end of the inner shaft extends axially out beyond the distal end of the second shaft; and v) a rotatable handle comprising a third axial bore extending along the longitudinal axis from a rotatable handle proximal end to a rotatable handle distal end, wherein the rotatable handle has a threaded inner surface that threading engages with the external threads of the second shaft, b) rotating the handle in a first direction to threadingly engage the rotatable threads with the external threads of the second shaft, thereby causing the rotatable handle to move proximally along the longitudinal axis against the radial pin and with the inner shaft moving in a proximal direction against the bias of the coiled spring while simultaneously moving a prosthesis threadingly engaged with the distal threaded end of the inner shaft into a contact relationship against the distal portion of the second shaft, c) inserting the prosthesis into a surgical site in a body, d) rotating the handle in a second, opposite direction, to threadingly disengage the rotatable threads from the external threads of the second shaft as the rotatable handle is moving distally along the longitudinal axis to thereby lessen the bias between the radial pin and the coil spring with the inner shaft supporting the prosthesis moving in a distal direction to release the contact relationship with the distal portion of the second shaft and the prosthesis, and e) rotating the fixed handle in the second direction to thereby rotate the second shaft against the axial pin connected to the inner shaft which consequently rotates the distal threads of the inner shaft from a threaded relationship with the prosthesis.

9. The method of claim 8 further comprising applying an impaction force against the fixed handle proximal end to help seat the prosthesis in the surgical site.

10. A kit comprising:
a) at least one surgical tool handle according to claim 1; and
b) a plurality of surgical tools adapted to be detachably connected to the tool handle; and
c) a case for organizing components of the kit.

11. A surgical tool handle, which comprises:
   a) a fixed handle comprising a first length extending along a longitudinal axis from a fixed handle proximal end to a fixed handle distal end, wherein an axial cavity extends along the longitudinal axis in a proximal direction from the fixed handle distal end at least part way along the first length thereof;
   b) a second shaft comprising a second length extending along the longitudinal axis from a second shaft proximal portion received in the axial cavity to a second shaft distal portion supporting an impactor head at a distal end thereof and extending out beyond the axial cavity of the distal end of the fixed handle, wherein the second shaft includes a first axial slot having a third length that is shorter than the second length with the slot, not extending to a distal end of the second shaft but extending inwardly from an outer surface thereof and being in open communication with a first axial bore extending to the distal end of the second shaft, wherein at least the second shaft distal portion has a threaded exterior surface;
   c) a coil spring received in an annular space provided between the outer surface of the second shaft proximal portion received in the axial cavity and an inner surface of the fixed handle;
   d) an inner shaft extending through the first axial bore in the second shaft from an inner shaft proximal end to a threaded distal end configured to support a prosthesis, wherein the proximal end of the inner shaft support a radial pin that is axially moveable along the slot in the second shaft such that when the radial pin biases against the coil spring, the distal threaded end of the inner shaft extends axially out beyond the impactor head of the second shaft; and
   e) a rotatable handle comprising a third axial bore extending from a rotatable handle proximal end to a rotatable handle distal end, wherein the rotatable handle has a threaded inner surface that threading engages with the external threads of the second shaft,
   f) wherein when the rotatable handle is rotated in a first direction with the rotatable threads threadingly engaging the external threads of the second shaft, the rotatable handle moves proximally to thereby cause the inner shaft to move in a proximal direction against the bias of the coiled spring and to simultaneously move the distal threaded end of the inner shaft closer to the impactor head of the second shaft, and
   g) wherein when the rotatable handle is rotated in a second, opposite direction, the rotatable threads threadingly disengage from the external threads of the second shaft as the rotatable handle moves distally to thereby lessen the bias between the radial pin and the coil spring so that threaded distal end of the inner shaft is movable in a distal direction to increase a distance between the impactor head of the second shaft and the distal threads of the inner shaft.

12. The surgical tool handle of claim 11 further comprising a strikeplate at the proximal end of the fixed handle.

13. The surgical tool handle of claim 11 wherein the intermediate shaft has a second axial slot that is diametrically opposed to the first axial slot and the radial pin is movable along both the first and second radial slots.

14. The surgical tool handle of claim 11 wherein the distal end of the intermediate shaft has a larger diameter than an inner diameter of the threaded inner surface of the rotatable handle.

15. A surgical tool handle, which comprises:
   a) a fixed handle comprising a first length extending along a longitudinal axis from a fixed handle proximal end to a fixed handle distal end, wherein an axial cavity extends along the longitudinal axis in a proximal direction from the fixed handle distal end at least part way along the first length thereof;
   b) a second shaft comprising a second length extending along the longitudinal axis from a second shaft proximal portion received in the axial cavity to a second shaft distal portion extending out beyond the axial cavity of the fixed handle and providing a distal impactor head, wherein the second shaft includes an axial slot having a third length that is shorter than the second length with the slot not extending to the distal end of the second shaft but extending inwardly from an outer surface thereof and being in open communication with an axial bore extending to the distal end of the second shaft, wherein at least the second shaft proximal portion has a threaded exterior surface;
   c) a coil spring received in an annular space provided between the outer surface of the second shaft proximal portion received in the axial cavity and an inner surface of the fixed handle;
   d) an inner shaft extending through the axial bore in the second shaft and from an inner shaft proximal end to a threaded distal end configured to support a prosthesis, wherein the proximal end of the inner shaft supports a radial pin which, in turn, supports a shaft ring surrounding the second shaft at the axial slot and wherein the radial pin is moveable along the axial slot in the second shaft such that when the shaft ring contacts the coil spring, the distal threaded end of the inner shaft extends axially out beyond the impactor head of the second shaft; and
   e) a rotatable handle comprising a third axial bore extending from a rotatable handle proximal end to a rotatable handle distal end, wherein the rotatable handle has a threaded inner surface that threading engages with the external threads of the second shaft,
   f) wherein when the rotatable handle is rotated in a first direction with the rotatable threads threadingly engaging the external threads of the second shaft, the rotatable handle moves proximally to thereby contact the shaft ring and cause the inner shaft to move in a proximal direction against the bias of the coiled spring and to simultaneously move the distal threaded end of the inner shaft closer to the impactor head of the second shaft, and
   g) wherein when the rotatable handle is rotated in a second, opposite direction, the rotatable threads threadingly disengage from the external threads of the second shaft as the rotatable handle moves distally to thereby release the bias between the shaft ring and the coil spring so that the inner shaft is movable in a distal direction to increase a distance between the impactor head of the second shaft and the distal threads of the inner shaft.

16. The surgical tool handle of claim 15 further comprising a strikeplate at the proximal end of the fixed handle.

17. The surgical tool handle of claim 15 wherein the intermediate shaft has a second axial slot that is diametrically opposed to the first axial slot and the radial pin is movable along both the first and second radial slots.

18. The surgical tool handle of claim 15 wherein the distal end of the intermediate shaft has a larger diameter than an inner diameter of the threaded inner surface of the rotatable handle.

* * * * *

UNITED STATES PATENT AND TRADEMARK OFFICE
CERTIFICATE OF CORRECTION

| | | |
|---|---|---|
| PATENT NO. | : 9,119,731 B2 | Page 1 of 1 |
| APPLICATION NO. | : 13/007735 | |
| DATED | : September 1, 2015 | |
| INVENTOR(S) | : Burgi et al. | |

It is certified that error appears in the above-identified patent and that said Letters Patent is hereby corrected as shown below:

On the title page item [73] delete "Greatbach Medical S.A." and insert --Greatbatch Medical S.A.--

In the claims

Column 8, line 25 Claim 8, line 33 after "against" delete ","

Column 9, line 15 Claim 11, line 15 after "slot" delete ","

Signed and Sealed this
Twenty-fourth Day of May, 2016

Michelle K. Lee
*Director of the United States Patent and Trademark Office*